US010049187B2

(12) United States Patent
Chait et al.

(10) Patent No.: US 10,049,187 B2
(45) Date of Patent: Aug. 14, 2018

(54) METHODS AND DEVICES FOR DETERMINING OPTIMAL AGENT DOSAGES

(71) Applicants: University of Massachusetts, Boston, MA (US); Analiza, Inc., Bay Village, OH (US)

(72) Inventors: Yossi Chait, Longmeadow, MA (US); Michael J. Germain, Hampden, MA (US); Christopher V. Hollot, Easthampton, MA (US); Joseph Horowitz, Amherst, MA (US); William Charles Vogt, Washington, DC (US)

(73) Assignees: University of Massachusetts, Boston, MA (US); Analiza, Inc., Cleveland, OH (US)

( * ) Notice: Subject to any disclaimer, the term of this patent is extended or adjusted under 35 U.S.C. 154(b) by 0 days.

(21) Appl. No.: 14/427,775

(22) PCT Filed: Sep. 12, 2013

(86) PCT No.: PCT/US2013/059360
§ 371 (c)(1),
(2) Date: Mar. 12, 2015

(87) PCT Pub. No.: WO2014/043295
PCT Pub. Date: Mar. 20, 2014

(65) Prior Publication Data
US 2015/0220700 A1 Aug. 6, 2015

Related U.S. Application Data

(60) Provisional application No. 61/701,527, filed on Sep. 14, 2012.

(51) Int. Cl.
| | | |
|---|---|---|
| *G01N 33/48* | (2006.01) | |
| *G06F 19/00* | (2018.01) | |
| *A61K 38/18* | (2006.01) | |
| *A61M 5/158* | (2006.01) | |
| *A61M 5/172* | (2006.01) | |
| *G16H 50/50* | (2018.01) | |
| *G06G 7/58* | (2006.01) | |

(52) U.S. Cl.
CPC ...... *G06F 19/3456* (2013.01); *A61K 38/1816* (2013.01); *A61M 5/158* (2013.01); *A61M 5/1723* (2013.01); *G16H 50/50* (2018.01); *A61M 2005/1726* (2013.01); *A61M 2205/3303* (2013.01); *A61M 2230/20* (2013.01)

(58) Field of Classification Search
CPC .......... G06F 19/18; G06F 19/22; G06F 19/24; G01N 33/666; G01N 33/582
See application file for complete search history.

(56) References Cited

U.S. PATENT DOCUMENTS

| | | | |
|---|---|---|---|
| 6,747,002 B2 | 6/2004 | Cheung et al. | |
| 7,232,797 B2 | 6/2007 | Farrell et al. | |
| 8,480,581 B2 | 7/2013 | Zhang et al. | |
| 9,852,267 B2 | 12/2017 | Gaweda et al. | |
| 2004/0157778 A1 | 8/2004 | Cheung et al. | |
| 2010/0113891 A1 | 5/2010 | Barrett et al. | |
| 2010/0249865 A1 | 9/2010 | Zhang et al. | |
| 2010/0331362 A1 | 12/2010 | Klaus et al. | |

FOREIGN PATENT DOCUMENTS

| | | |
|---|---|---|
| WO | WO 2008/020043 A1 | 2/2008 |
| WO | WO 2011/057744 A1 | 5/2011 |
| WO | WO 2011/082421 A1 | 7/2011 |
| WO | WO 2013/049624 A1 | 4/2013 |

OTHER PUBLICATIONS

International Search Report and Written Opinion dated Nov. 5, 2013 in connection with Application No. PCT/US2013/059360.
International Preliminary Report on Patentability dated Mar. 26, 2015 in connection with Application No. PCT/US2013/059360.
Brier et al., Randomized trial of model predictive control for improved anemia management. Clin J Am Soc Nephrol. May 2010;5(5):814-20. doi: 10.2215/CJN.07181009. Epub Feb. 25, 2010.
Brier et al., Predictive modeling for improved anemia management in dialysis patients. Curr Opin Nephrol Hypertens. Nov. 2011;20(6):573-6. doi: 10.1097/MNH.0b013e32834bba4e.
Gaweda et al., Using clinical information in goal-oriented learning. IEEE Eng Med Biol Mag. Mar.-Apr. 2007;26(2):27-36.
Gaweda et al., Model predictive control of erythropoietin administration in the anemia of ESRD. Am J Kidney Dis. Jan. 2008;51(1):71-9.
Gaweda et al., Individualized anemia management reduces hemoglobin variability in hemodialysis patients. J Am Soc Nephrol. Jan. 2014;25(1):159-66. doi: 10.1681/ASN.2013010089. Epub Sep. 12, 2013.
Germain et al., The engineering of anemia management protocols in chronic kidney disease. American Society of Nephrology 43$^{rd}$ Annual Meeting and Scientific Exposition. Nov. 18-21, 2010.
Lines et al., A predictive algorithm for the management of anaemia in haemodialysis patients based on ESA pharmacodynamics: better results for less work. Nephrol Dial Transplant. Jun. 2012;27(6):2425-9. doi: 10.1093/ndt/gfr706. Epub Dec. 29, 2011.
Nichols et al., Simplification of an erythropoiesis model for design of anemia management protocols in end stage renal disease. Conf Proc IEEE Eng Med Biol Soc. 2011;2011:83-6. doi: 10.1109/IEMBS.2011.6089902.

(Continued)

*Primary Examiner* — Eric S Dejong
(74) *Attorney, Agent, or Firm* — Wolf, Greenfield & Sacks, P.C.

(57) ABSTRACT

The present invention is generally directed to methods and devices for determining dosing for a medical agent. In some embodiments, a mathematical algorithm is employed for computing erythropoiesis-stimulating agents dosing for treating anemia in a subject, e.g., a human subject. Any suitable dosing may be used, e.g., intravenous, subcutaneous, or oral dosing. In some cases, dosing for a wide range of subject types and health conditions can be achieved using the devices and methods disclosed herein.

24 Claims, 14 Drawing Sheets

(56) References Cited

OTHER PUBLICATIONS

Nichols, Modeling erythropoiesis for anemia management protocol design: A capstone manuscript. Dec. 2010:1-30.
Rogers et al., Evaluation of anemia management by algorithms in patients with chronic kidney disease who are not receiving dialysis. Can J Hosp Pharm. Mar. 2011;64(2):141-6.
Vogt, Feedback-control-based-design of dosage protocol for administering recombinant human erythropoietin in treating anemia in chronic renal disease: A capstone manuscript. May 2009:1-51.
European Office Action for Application No. EP 13 766 198.9 dated Feb. 12, 2018.
Atkinson et al., Numerical solution of ordinary differential equations. In: Numerical Solution of Ordinary Differential Equations: Atkinson/Numerical, Jan. 27, 2009, John Wiley & Sons, Inc. Hoboken, NJ, USA. 261 pages.
Mustafa Inc. et al., A comparison of numerical ode solvers based on Euler methods, Jan. 1, 1998, pp. 153-159. Retrieved from the Internet: http://mdpi.com/2297-8747/3/3/153/pdf. Retrieved on Feb. 5, 2018.
European Office Action for Application No. EP 13766198.9, dated Apr. 24, 2015.
European Office Action for Application No. EP 13766198.9, dated Jun. 9, 2017.

FIG. 7

| Responsiveness Category | Protocol | Hgb Mean (SD) (g/dL) | Hgb in-Range [10-12] mean (SD) (%) | Weekly EPO Mean (SD) (IU) |
|---|---|---|---|---|
| All categories | New | 11.08 (0.10) | 80 (8) | 12834 (10184) |
|  | current | 10.81 (0.39) | 73 (17) | 14492 (13726) |
| Very Hyper | New | 11.08 (0.10) | 79 (9) | 2197 (764) |
|  | current | 10.81 (0.39) | 72 914) | 2318 (1122) |
| Hyper | New | 11.08 (0.08) | 81 (7) | 2878 (519) |
|  | current | 10.92 (0.45) | 66 (9) | 3491 (1305) |
| Intermediate | New | 11.09 (0.05) | 79 (10) | 6650 (2649) |
|  | current | 10.79 (0.35) | 74 (15) | 7422 (2984) |
| Hypo | New | 11.10 (0.12) | 80 (7) | 20703 (8870) |
|  | current | 10.83 (0.43) | 73 (19) | 23439 (14612) |

METHODS AND DEVICES FOR DETERMINING OPTIMAL AGENT DOSAGES

RELATED APPLICATIONS

This application is a national stage filing under 35 U.S.C. § 371 of International Application No. PCT/US2013/059360, filed Sep. 12, 2013, by Chait, et al., which claims the benefit of U.S. Provisional Patent Application Ser. No. 61/701,527, filed Sep. 14, 2012, by Chait, et al., each of which is incorporated herein by reference.

FIELD

The present invention, in some embodiments thereof, relates to methods and devices for effectively determining an optimal dosage program for a medical agent. The instant invention, in some embodiments, allows for such determinations with algorithms that applicable to subjects from a wide range of ages and racial backgrounds.

BACKGROUND

Blood is critical for human health. Red blood cells move carbon dioxide out of and oxygen into metabolizing cells throughout the body. The key component for this action is the protein hemoglobin. Hemoglobin, a tetrameric iron protein, is produced according to the biological needs of the body and moves throughout the body in red blood cells. In some cases, the body is unable to produce enough red blood cells, e.g., due to some form of illness that may include renal failure. Such conditions can be extremely dangerous, as the brain in particular has a high oxygen demand.

Erythropoietin (EPO) is a critical material in the production of red blood cells. EPO is produced in the renal cortex. EPO was also one of the first recombinant drugs to receive FDA approval and find wide use. However, methods and devices for effectively delivering EPO to a needy patient are critical. Optimization of EPO and similar drug delivery can enhance the quality of life for those who cannot produce EPO on their own, and efficient dosing of EPO can save enormous amounts of money for a health provider such as an HMO or hospital.

The prior art generally describes delivery of EPO to anemic patients in a manner that is case-specific and requires frequent dosing. However, many current anemia management protocols (or AMPs) fail to stabilize hemoglobin concentrations in a subject, which may lead to adverse medical complications or even death of the subject. Accordingly, improvements in such delivery and control are needed.

SUMMARY

The present invention, in some embodiments thereof, relates to methods and devices for effectively determining an optimal dosage program for a medical agent. The subject matter of the present invention involves, in some cases, interrelated products, alternative solutions to a particular problem, and/or a plurality of different uses of one or more systems and/or articles.

One aspect of the present invention is generally directed to methods for determining optimal dosing of erythropoiesis agents for an anemic subject.

In another aspect, the present invention is generally directed to a method for computing erythropoiesis-stimulating agents (ESAs) dosing (e.g., intravenously, subcutaneously, orally, etc.), for treating anemia in a subject, such as a human subject. In some cases, the method includes acts of measuring a value of at least one biochemical property related to an anemia status in the subject; determining a difference between the value of the at least one biochemical property and a predetermined optimal value for the property; and, employing a computing element with a mathematical algorithm to calculate a required ESA dosage based on the difference. In some cases, the algorithm may maintain predetermined target performance criteria for a range of biochemical property values in a plurality of predetermined physiological factors affecting the value of the at least one biochemical property.

In one set of embodiments, the biochemical property is hemoglobin concentration.

In another set of embodiments, the range of target values is 8 g/dl and 14 g/dl

In another set of embodiments, the dosing involves administration of recombinant human erythropoietin (rHuEPO).

In another set of embodiments, the rHuEPO is produced in a non-human source using synthetically or biologic methods.

In another set of embodiments, the dosing involves administration of novel erythropoiesis stimulating protein (NESP).

In another set of embodiments, the dosing involves administration of HIF stabilizing agent.

In another set of embodiments, the value is determined 3 times a week, once a week, bi-weekly, monthly, or other intervals.

In another set of embodiments, the anemia is associated with renal failure.

In another set of embodiments, the physiological factors include red blood cell lifespan, production rate of new red blood cells, and iron status.

In another set of embodiments, the physiological factors include intravenous, subcutaneous, or oral delivery of iron to the subject.

The present invention additionally includes, in another aspect, a method for applying an anemia management protocol (AMP) for treating anemia in a subject, such as a human subject. For example, in certain methods, the method includes acts of measuring a value of at least one biochemical property related to an anemia status in the subject; determining a difference between the value of the at least one biochemical property and a predetermined value for the property; and, employing a computing element with a mathematical algorithm to calculate a required dosage for erythropoiesis-stimulating agents (ESA) based on the difference. In some cases, the algorithm may include a step for reducing the sensitivity of the anemia management protocol to variability in the subject's responsiveness to the erythropoiesis-stimulating agents.

In one set of embodiments, the algorithm includes a step to reduce the sensitivity of the AMP to variations in concentrations of iron and vitamins in the subject's blood.

In another set of embodiments, the algorithm includes a step for reducing the sensitivity of the AMP to variability in the value of the biochemical property.

In another set of embodiments, the algorithm includes a step for adjusting the gain of the AMP for a present level of the subject's responsiveness to the ESA.

In another set of embodiments, the algorithm includes a step for calculating dosage for the ESA for the subject over a predetermined dosing schedule.

In another set of embodiments, the predetermined dosing schedule is selected from the following: daily, three times per week, weekly, bi-weekly, and monthly.

In another set of embodiments, the step includes an integrator or an approximated discrete-time integrator.

In another set of embodiments, the AMP remains fixed for any target values of the property in the range 8 g/dl and 14 g/dl In another set of embodiments, the integrator is described by the equation:

$$\frac{z}{z-1},$$

and the approximated discrete-time integrator is described by:

$$\frac{z}{z-a},$$

wherein the value of a is near 1.

In another set of embodiments, the discrete-time integrator is selected from the following: Forward Euler, Backward Euler, Trapezoidal method, second-order accurate method, or third order accurate method.

In another set of embodiments, the algorithm includes at least one step for reducing the sensitivity of the AMP to variability in the value of the measured biochemical property.

In another set of embodiments, the algorithm includes an estimator for the subject's responsiveness to ESAs.

In another set of embodiments, the estimator of the property is described by the following equation:

$$\text{estimated } responsivenss = \frac{\text{mean(weekly } Hgb \text{ measurements during past } n \text{ weeks)}}{\text{mean(weekly } ESA \text{ doses during past } n \text{ weeks)}}.$$

In another set of embodiments, the gain associated with the AMP is adjustable in an inversely proportional manner to the responsiveness.

The present invention, in yet another aspect, is generally directed to a device for delivering erythropoiesis-stimulating agents (ESA) to a subject, such as a human subject. In some cases, the erythropoiesis-stimulating agents may be an optimized amount. The erythropoiesis-stimulating agents may be delivered by any suitable technique, for example, intravenously, subcutaneously, orally, etc. In some cases, the erythropoiesis-stimulating agents may be delivered by the device for treating anemia in the subject, In one set of embodiments, the device includes one or more of a measuring element adapted to measure a value of at least one biochemical property related to an anemia status in the subject; a communication element adapted to communicate the value to a computing element; a computing element adapted to calculate a difference between the value of the at least one biochemical property and a predetermined value or range of values for the property, the element adapted to employ a mathematical algorithm to calculate a required ESA dosage based on the difference. In some cases, the algorithm may remain fixed for any target values of the property in the range 8 g/dl and 14 g/dl and, a delivery element for delivering the ESA to the subject.

In another set of embodiments, the erythropoiesis-stimulating agents include EPO.

In another set of embodiments, the delivery element is implanted in the subject.

In another set of embodiments, the communication element includes a wireless component.

In another set of embodiments, the measuring element includes a disposable component.

In another set of embodiments, the computing element is selected from laptop computer, tablet computer, cell phone, table-top computer, networked computing device, and wireless computing device.

The present invention, in yet another aspect, is directed to a method for applying an anemia management protocol (AMP) for treating anemia in a human subject, including: measuring a value of at least one biochemical property related to an anemia status in the subject; determining a difference between the value of the at least one biochemical property and a predetermined value for the property; and, employing a computing element with a mathematical algorithm to calculate a required dosage for erythropoiesis-stimulating agents based on the difference. The algorithm may include an integrator or an approximated discrete-time integrator, the integrator being described by the equation:

$$\frac{z}{z-1},$$

and the approximated discrete-time integrator being described by:

$$\frac{z}{z-a},$$

wherein the value of a is near 1.

In another aspect, the present invention is directed to a method. In one set of embodiments, the method includes acts of determining a hemoglobin concentration in a subject; using a device comprising a controller comprising an integrator or an approximated discrete-time integrator, and encoding Equations 1-5, to determine a dosage of an erythropoiesis-stimulating agent; and administering the dosage to the subject.

The present invention, in still another aspect, is directed to a device. In one set of embodiments, the device comprises a receiver for determining a hemoglobin concentration in a subject; a controller comprising an integrator or an approximated discrete-time integrator, and encoding Equations 1-5 to determine a dosage of an erythropoiesis-stimulating agent using the hemoglobin concentration; and an applicator for administrating the dosage to the subject. In another set of embodiments, the device comprises a receiver for determining a hemoglobin concentration in a subject; and a controller comprising an integrator or an approximated discrete-time integrator, and encoding Equations 1-5 to determine a dosage of an erythropoiesis-stimulating agent using the hemoglobin concentration.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 7 shows a table comparing performance of a prior art protocol and a protocol based on an embodiment of the instant invention.

DETAILED DESCRIPTION

Figure 1:
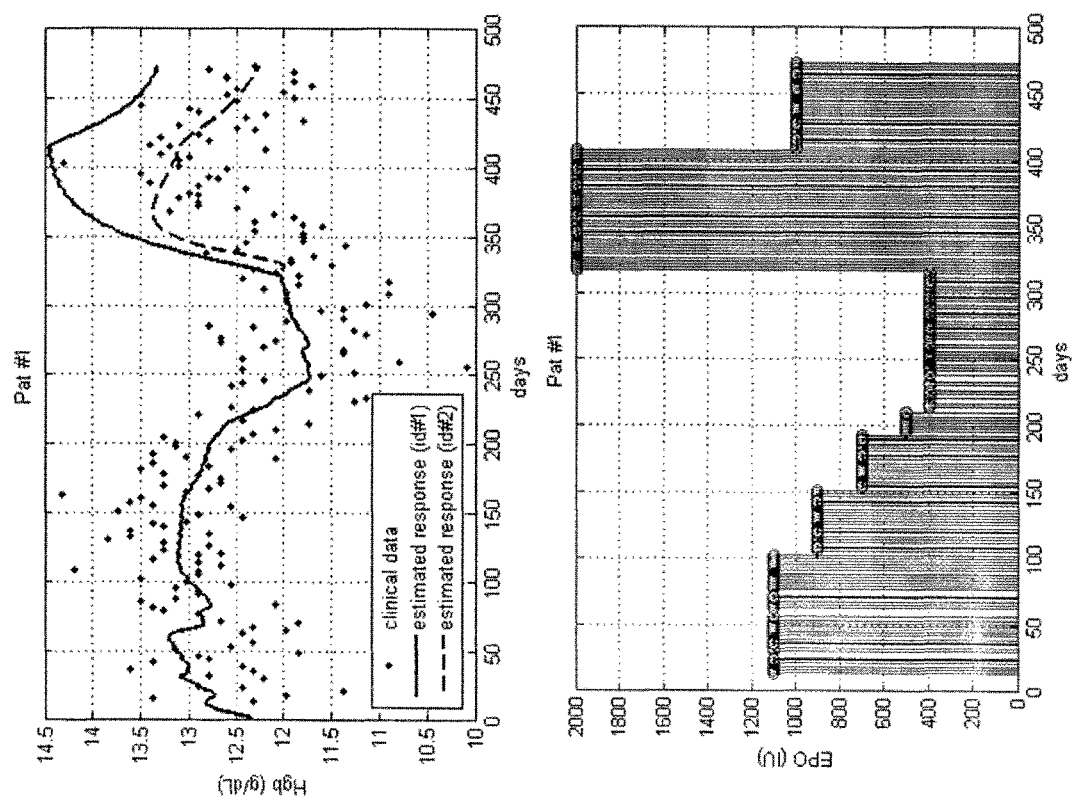
FIG. 1 shows simulated Hgb (hemoglobin) responses of a subject (Pat #1) vs. clinical Hgb data.

The present invention is generally directed to methods and devices for determining dosing for a medical agent. In some embodiments, a mathematical algorithm is employed for computing erythropoiesis-stimulating agents dosing for treating anemia in a subject, e.g., a human subject. Any suitable dosing may be used, e.g., intravenous, subcutaneous, oral, intraarterial, intramuscular, transdermal, etc. In some cases, dosing for a wide range of subject types and health conditions can be achieved using the devices and methods disclosed herein.

It should be noted that various embodiments of the invention are generally directed to devices and methods able to control the concentration of hemoglobin in a subject via the administration of erythropoiesis-stimulating agents such as erythropoietin. By using the equations as discussed herein, a device may be able to calculate and in some cases administer a next dose of erythropoiesis-stimulating agent that is to be applied to the subject in a way such that the concentration of hemoglobin within the subject remains controlled. Such a dosing can only be accurately determined using equations as are discussed herein, although the devices and methods as discussed herein are generally directed to controlling hemoglobin concentrations within the blood of a subject, not to the mathematical equations themselves. In addition, control of the concentration of hemoglobin within the blood is of real, concrete, palpable, tangible, and critical use in maintaining the health of subjects, e.g., having or at risk of anemia; the failure to control such hemoglobin concentrations within the subject could potentially lead to adverse medical complications or even death of the subject. For example, as is described herein, the application of proper doses of an erythropoiesis-stimulating agent, such as erythropoietin, to a subject can often be of critical importance in transforming the health of the subject, and potentially avoiding adverse medical complications or death of the subject.

For example, in one set of embodiments, the present invention is generally directed to determining an optimal dosing of an erythropoiesis-stimulating agent (ESA) such as EPO (erythropoietin) or OMONTYS for a subject, for example, an anemic patient. In some cases, the present invention may allow for optimized use of the ESA while providing optimal hemoglobin (Hgb) concentration in subjects, e.g., by treating the subjects using the devices and methods as discussed herein.

Erythropoietin (EPO), secreted primarily by the kidneys (e.g., in response to hypoxia), drives the production of red blood cells (RBCs) by stimulating the production of the RBC progenitors within the bone marrow. In certain conditions, e.g., chronic kidney disease (CKD), endogenously produced EPO is insufficient to maintain normal RBC concentrations, which may lead to a clinical state of anemia. One example of an erythropoietin that can be applied to a subject is recombinant human EPO. The discovery of recombinant human EPO (rHuEPO) has shifted the treatment of anemia for subjects on dialysis from blood transfusions to rHuEPO therapy. Although more than 20 years have passed since the discovery of rHuEPO, effectively computing the dose size and frequency of rHuEPO applications in order to maintain the desired mean concentration and to minimize variations of Hgb a direct indictor of RBC mass has not been described by others.

Although not wishing to be bound by any theory, the following model is implemented in various devices and methods in accordance with certain embodiments of the invention. As noted below, certain Anemia Management Protocols (AMP) for treating anemia in a subject are implemented by acquiring a sample from the subject, determining a concentration of hemoglobin in the sample, using the model to determine the next dose of a suitable erythropoiesis-stimulating agent to be applied to the subject, and optionally applying the next dose to the subject. In some cases, the model may be implemented, e.g., using an integrator or an approximated discrete-time integrator to determine certain parameters of the model, as those parameters cannot be precisely solved, and can only be numerically evaluated using a computer, e.g., via numerical integration. Thus, a computer or other integration device is typically required in order to determine the next dose of the erythropoiesis-stimulating agent.

The dynamics of hemoglobin concentration following the administration of intravenous (IV) EPO or another suitable erythropoiesis-stimulating agent can be described using a combination of pharmacokinetic (PK) and pharmacodynamics (PD) models, which are outlined as follows. It should be noted that this model is applied in certain embodiments of the invention, although in some embodiments, other equivalent models may be used to relate hemoglobin to an erythropoiesis-stimulating agent. For example, in some embodiments, a model substantially similar to the following, but adding or subtracting one or more correction terms, may be used, and such modifications may be considered to fall within the scope of the equations outlined as follows.

The PK model outlined as follows comprises a single dynamic pool of EPO, an IV EPO dose as an impulsive input, and a saturable function capturing nonlinear clearance/degradation as shown below. The kinetics of the exogenous EPO, E, is described by the following nonlinear equation:

$$\frac{d}{dt}E(t) = -\frac{V_{max}E}{K'_m V_d + E} + d(t), \quad (1)$$

where $V_{max}$ denotes maximal clearance/degradation rate of EPO within a subject (e.g., via the kidneys), $K_m \approx K'_m V_d$ denotes the concentration of rHuEPO which produces the half maximal clearance rate of $V_{max}$ in the subject, $V_d$ denotes the volume of distribution of EPO in blood, $K'_m$ denotes the concentration of rHuEPO which produces half maximal E clearance rate of $V_{max}$ in the subject, and d denotes the rHuEPO dose as a function of time. rHuEPO is used in this model as an example of an erythropoiesis-stimulating agent, although in other embodiments of the invention, other erythropoiesis-stimulating agents may be used, e.g., in addition or instead of rHuEPO. For example, this model can be used for any ESA whose mechanism of action is simulation via EPOR (EPO) receptor.

This model for subcutaneous administration of EPO includes an additional term capturing the absorption process. The total amount of EPO is the sum of exogenous and endogenous levels:

$$E_p = E + E_{en} \quad (2),$$

where $E_{en}$ denotes the baseline level of endogenous EPO, E denotes the baseline level of exogenous EPO, and $E_p$ is the total amount of EPO present in the subject.

The PD model comprises stimulatory effects of EPO on differentiation, maturation, and proliferation of hematopoietic stem cells into reticulocytes and maturation into red blood cells. The stimulatory effect of the blood EPO level on the production of new reticulocytes is described by a nonlinear, time-delayed function (indicated by the term $T_D$):

$$k_{in}(t - T_D) = \frac{S_{max} E_P(t)}{SC'_{50} V_d + E_P(t)}, \quad (3)$$

where $k_{in}$ is the production rate of new reticulocytes in the subject (offset by a time-delay $T_D$), $S_{max}$ is the maximal stimulation rate of new reticulocytes, $SC_{50} \approx SC'_{50}'V_d$ denotes the concentration of EPO which produces a half maximal production rate of new reticulocytes in the subject ($SC'_{50}$ denotes the concentration of EPO which produces half maximal production rate and $V_d$ denotes the volume of distribution of EPO in blood), and $T_D$ (or $t_D$) is the time required for pluripotent hematopoietic stem cells to become RBCs (i.e., the progression of the stem cells through burst-forming units, colony-forming units, erythroblasts, and reticulocytes). It should be noted that these equations are nonlinear and therefore cannot be explicitly solved, but instead can only be evaluated numerically. In addition, many of the constants described above can be estimated using many available identification algorithms based on clinical EPO and Hgb time series.

The RBC pool dynamics is described by the following differential equation:

$$\frac{d}{dt}RBC(t) = k_{in}(t - t_D) - \int_0^\infty k_{in}(t - t_D - \lambda)l_{RBC}(t - \lambda, \lambda)d\lambda, \quad (4)$$

where RBC (t) is the mass of red blood cells (which the reticulocytes mature into), $l_{RBC}(l,t)$ is the probability density function of the lifespan t of an RBC entering the pool at time l (in the above integral, $l=t-\lambda$ and $t=\lambda$), and $t_D=T_D$ is the time required for pluripotent hematopoietic stem cells to become RBCs. In addition, $k_{in}$ is the production rate of new reticulocytes in the subject (offset by a time-delay $t_D$), as described in Equation 4. As is discussed herein, this equation may be evaluated in some embodiments using an integrator or an approximated discrete-time integrator.

Finally, the concentration of hemoglobin is assumed fixed with respect to the concentration of red blood cells in the subject:

$$Hgb = K_{Hgb}RBC \quad (5),$$

where RBC is the mass of red blood cells, and $K_{Hgb}$ is the average hemoglobin concentration per RBC, also known as the mean corpuscular hemoglobin (MCH).

Accordingly, based on the above equations, starting with a known dose of erythropoietin or another suitable erythropoiesis-stimulating agent (e.g., such as OMONTYS), and adding in known or determinable constants such as $V_{max}$ and $K'_m$, the concentration of hemoglobin in a subject may be determined. Conversely, if a specific hemoglobin amount or concentration is desired in a subject, the above equations may be used to determine the next dose of a erythropoiesis-stimulating agent to give to the subject.

In one set of embodiments, a device comprising a controller is used to predict a hemoglobin concentration or amount in a subject based on a dose of an erythropoiesis-stimulating agent given to the subject. For example, the prediction may be made for a future moment in time, or used to determine the success or failure of a concurrently occurring treatment. In another set of embodiments, a device comprising a controller is used to determine a suitable dose of an erythropoiesis-stimulating agent to be given to a subject based on a desired hemoglobin concentration or amount.

These calculations may be performed by a device comprising a controller with appropriate hardware and/or software, e.g., for numerically evaluating the above equations, e.g., as discussed herein. It should be noted that these equations, in total, require mathematical operations such as numerical integration of probability density functions, which cannot be precisely solved, but can only be numerically evaluated using a computer, e.g., using computational discrete-time integrator methods such as the Forward Euler, Backward Euler, Trapezoidal method, second-order accurate methods, or third order accurate methods. Accordingly, it is generally not possible for a human to evaluate these equations with a sufficient degree of accuracy, and thus, a device comprising a controller such as is described herein is used to numerically evaluate the above equations, in various embodiments.

Accordingly, in one aspect, the present invention is generally directed to devices and methods for treating a subject with serial doses of an erythropoiesis-stimulating agent (ESA). In one set of embodiments, the concentration of hemoglobin in a subject is determined, directly or indirectly, and by using techniques such as those described herein, the next dose of the erythropoiesis-stimulating agent to be given to the subject is then computed or calculated.

One non-limiting example of an ESA is erythropoietin. Erythropoietin is made endogenously by a subject, and can also be obtained commercially (e.g., as recombinant human erythropoietin); in some cases, the subject may receive erythropoietin from both sources, which need to be balanced against each other as is discussed herein. For example, erythropoietin may be produced by recombinant DNA technology in mammalian cell culture. Recombinant EPO has a variety of glycosylation patterns giving rise to alpha, beta, delta, and omega forms, for example Epogen, Procrit, and Anserp, made by Amgen. In one embodiment, the erythropoietin given to the subject is recombinant human erythropoietin (rHuEPO).

Another example of an ESA is OMONTYS (peginesatide). OMONTYS is a synthetic, pegylated, peptide-based ESA that mimics the structure of erythropoietin. Yet other non-limiting examples of ESAs are hypoxia-inducible factors (HIFs), transcription factors that respond to decreases in oxygen, or hypoxia, in the cellular environment. Several companies, for example Akebia Therapeutics and Fibrogen, are currently involved in clinical trials that study the therapeutic potential of these inhibitors in treating patients with anemia of chronic disease.

The subject may be one in which it is desired to control or normalize hemoglobin concentrations. The subject may be human or non-human, e.g., a non-human mammal. The subject may be anemic, for example, due to chronic kidney disease (e.g., where the subject may or may not be on dialysis), chemotherapy, or the effects of zidovudine (AZT) and other medications used to treat HIV infection (which often cause anemia as a side effect).

One set of embodiments is generally directed to a device for delivering erythropoiesis-stimulating agents to a subject. Typically, a sample (e.g., of blood) from the subject is acquired and analyzed (e.g., as discussed herein) to determine the concentration of hemoglobin in the sample. Other biochemical properties may also be determined, in addition or instead of hemoglobin in the sample, for example, complete blood count, soluble EPO receptors (sEPOR), iron test, and Ferritin, which may be used to estimate hemoglobin concentrations using routine techniques known to those of ordinary skill in the art. These properties may be determined, and in some cases, used to estimate the concentration of hemoglobin, e.g., for use in the equations described herein. Typically, serial samples are taken from the subject. For example, the samples may be taken daily, weekly, biweekly, every 4 weeks, monthly, etc. In some cases, however, the samples are taken more frequently, e.g., hourly or every few hours.

FIG. 1 shows the applicability of Equations 1-5 to predict Hgb response of a chronic kidney disease subject ("Pat #1") to EPO administration, as an illustrative non-limiting example. Specifically, FIG. 1 shows two predicted Hgb responses of the subject based on Equations 1-5 vs. the clinical data (top), and the administered EPO doses (bottom). It is observed that the first set of estimated parameters (id#1) successfully predicted the clinical Hgb response up to day 325 (approximately), but failed to do so thereafter. This required a second set of parameters (id#2) to be estimated for the remaining period from day 325 to day 473. Most subjects undergo changes in erythropoiesis over time resulting in a time-varying model using Equations 1-5. Such commonplace changes render protocols based on open-loop models inefficient. In other words, without the presence of a controller (as discussed below) to discretize and implement an integrator or an approximated discrete-time integrator, Equations 1-5 as discussed above may not adequately be used to predict hemoglobin concentrations in the subject, or future doses of a suitable erythropoiesis-stimulating agent to be applied to the subject, as is discussed herein. It should also be noted that, as discussed herein, some of the controllers discussed herein are robust and able to respond to disturbances in the subject, e.g., bleeding, cancer, bacterial infections, blood transfusions, etc. that Equations 1-5 are otherwise unable to incorporate.

Accordingly, in one set of embodiments, a device comprising a controller is used to regulate the concentration or amount of hemoglobin (Hgb) in a subject. The controller may accept input based on a dosage of an ESA given to a subject, and be used to determine the concentration or amount of hemoglobin, or the controller may accept input based on a desired concentration or amount of hemoglobin (Hgb), and be used to determine a suitable dosage of an erythropoiesis-stimulating agent that would produce such as a result. In some embodiments, other biochemical properties may also be determined, in addition or instead of hemoglobin, as discussed herein, and such properties used instead of or in addition to the desired concentration or amount of hemoglobin, e.g., in the equations discussed above.

One objective, in certain embodiments of the invention, of an anemia management protocol (AMP), i.e., a controller (in the terminology of control engineering), is to regulate hemoglobin (Hgb) concentrations to remain within a desired range, minimization of over- and/or under-shoot, and/or to moderate changes in response due to disturbances in the subject. Examples of such disturbances that may be taken into account in the controller include, bleeding, cancer, bacterial infections, blood transfusions, or the like, that may alter the availability of hemoglobin in the subject and/or the amount of oxygen delivery that is available due to changes in hemoglobin concentrations, either positively or negatively (in contrast, prior art protocols, e.g., using dose-response predictions, are typically incapable of accounting for such disturbances). In robust control methods, a single controller is designed based on a nominal model, a quantitatively defined model uncertainty, and the desired performance. In this context, an estimated model can be considered a nominal model, at least in certain embodiments of the invention. One then may group subjects into several groups, for example based on the amount of EPO required to achieve the desired Hgb concentration. Within each such group, one defines a range for each parameter that includes all likely values for subjects in that group. This defines a model uncertainty. Desired performance parameters can include, for example, minimal overshooting of Hgb response, reduced cycling, and maintenance of Hgb within a specified range.

Figure 2:
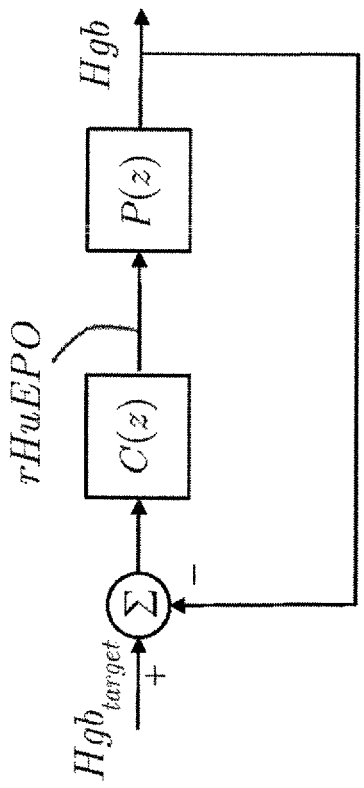
FIG. 2 shows a block diagram of a discreet feedback control system for one embodiment of the instant invention.
Figure 3:
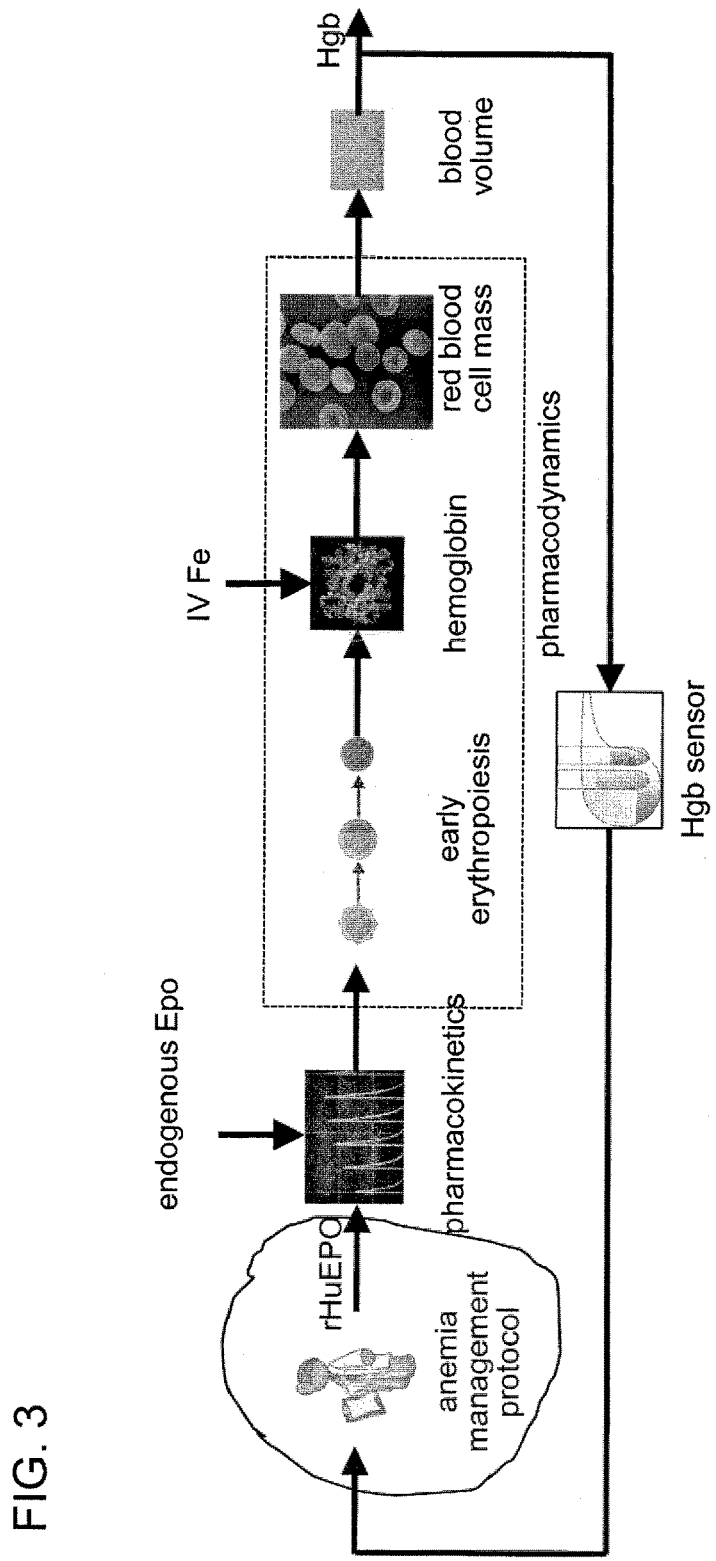
FIG. 3 shows a schematic view of one example of AMP design.

There are several options available for the design of the controller. One approach is to discretize the model based on the dosing protocol, weekly as an example. A block diagram of the discrete-time system is shown in FIG. 2 as an illustrative non-limiting example. It includes the following components: a protocol (e.g., a discrete-time controller protocol) C(z) operating once per dose decision period (T), whose input signal is the difference between target Hgb and actual Hgb and output is the dose of an ESA, and the discrete-time plant P(z) representing the dynamics between administered ESA doses and resulting Hgb (for example, the continuous-time plant may be described herein by Equations 1-5, as noted above).

Thus, in one embodiment of the present invention, a controller may comprise a discrete-time controller protocol (C(z)) and a plant P(z). It should be noted, however, that the present invention is not limited only to the controller as is shown in FIG. 2. In other embodiments of the invention, other blocks may be present, and/or the blocks may be arranged in a different order.

As a non-limiting example, as is shown in FIG. 2, the difference between the target and actual concentrations of hemoglobin is applied to a discrete-time controller protocol (C(z)) to determine a suitable level of an ESA (such as rHuEPO as is shown in FIG. 2) that is to be applied to a subject, then that level of the ESA is applied to the plant model (P(z)) (e.g., as is implemented using Equations 1-5 to determine the concentration of hemoglobin (Hgb) that will be present in the subject at the next period of time T.

Non-limiting examples of controller protocols (C(z)) are discussed below. However, in general, the discrete-time controller protocol may proceed by using the current input signal (for example, hemoglobin concentration), and the previous input and output signals to determine the next output signal (e.g., the amount of an erythropoiesis-stimulating agent that is required). A variety of different controller protocols may be used, as is discussed herein. For example, in some embodiments, an estimation of the responsiveness in a subject between the amount of erythropoiesis-stimulating agent that is administered to the subject and the resulting hemoglobin concentration may be used within the controller. This relationship may be termed the gain. Thus, in one set of embodiments, the controller may comprise a discrete-time controller protocol that uses the gain as the input. The gain may be set to a fixed constant, e.g., based on the subject's use of an erythropoiesis-stimulating agent, or the gain may be estimated using measurements or samples taken from a subject, e.g., at different points in time.

The computations required by the controller (e.g., to implement an anemia management protocol) may be performed using a device having these equations encoded in hardware and/or software. At that later point in time, in some embodiments of the invention, the device may also administer that dosage, e.g., intravenously, subcutaneously, orally, etc. For example, the device may be wristwatch or other portable device that is able to receive a sample of blood, calculate the next dose using a controller, as discussed herein, and apply the next dose to the subject at the appropriate time. The device, in certain embodiments, may include a hemoglobin sensor that can determine the hemoglobin concentration from the sample of blood, e.g., using pulse oximetery (reflectance or transmissive) sensors, spectrophotometric sensors, electrochemical sensors, or the like. Many such hemoglobin sensors may be readily obtained commercially. In addition, in one set of embodiments, the device may further comprise a needle and a reservoir for containing a suitable erythropoiesis-stimulating agent. Thus, for example, upon receiving a determination of the concentration of hemoglobin in a subject, the controller may determine an appropriate dosage of a suitable erythropoiesis-stimulating agent, and the device may then deliver that dosage of the erythropoiesis-stimulating agent from the reservoir via the needle.

As mentioned, the device may also include a receiver for determining the hemoglobin concentration in a subject. For instance, the receiver may include a hemoglobin sensor for determining hemoglobin in a sample of blood withdrawn from the subject (e.g., as discussed herein), or the receiver may include an input device for entering a concentration of hemoglobin (for example, if an external device was used to determine the concentration of hemoglobin in a sample of blood withdrawn from the subject. As various examples, the input device may include a keyboard (e.g., for manual entry of the hemoglobin concentration), or a USB port, a transceiver, etc. that allows the input device to receive input from a computer or other external device.

The biochemical property most usually measured is the concentration of hemoglobin, although other properties could also be used in other embodiments. Deviations from target hemoglobin concentration allow for determination of appropriate ESA dosing for a subject. In some embodiments, the algorithm allows for predetermined target performance in spite of potential disturbances—such as bleeding, cancer, bacterial infection, blood transfusions, or the like—that may lead to changes in the amount of blood and/or changes in the amount of oxygen delivery to organs within the subject, e.g., due to changes in hemoglobin concentrations. Other potential disturbances include, but are not limited to, levels of B12 and folate, iron availability, inflammation, uremic toxins, hypothyroidism, hypersplenism, ongoing infection, etc.

Most clinicians rely on an expert system comprising a set of rules based on past experience and retrospective studies. From the clinician's viewpoint, this approach is practical; it relies on a few, readily-available measurements, and is applicable to the entire population. Indeed, a necessary factor in designing a therapeutic protocol is to understand the biological dynamics. Pharmacokinetic/pharmacodynamics (PK/PD) studies help to predict Hgb response to rHuEPO dosing, and to develop open-loop models of this causal relationship. However, as is discussed herein, when dosing of an erythropoiesis-stimulating agent (ESA) such as rHUEPO is based on Hgb concentrations, the response is that of a closed-loop system. In other words, the relationship between the ESA and the resulting Hgb concentration cannot be inferred from the open-loop PK/PD studies that are commonly used by others. In contrast, as is discussed herein, various embodiments are used to predict Hgb concentrations in a subject, by analyzing the closed-loop system formally (e.g., with a controller), explicitly taking into account the periodicity of the protocols and the uncertain parameters of the PK/PD models.

Figure 4:
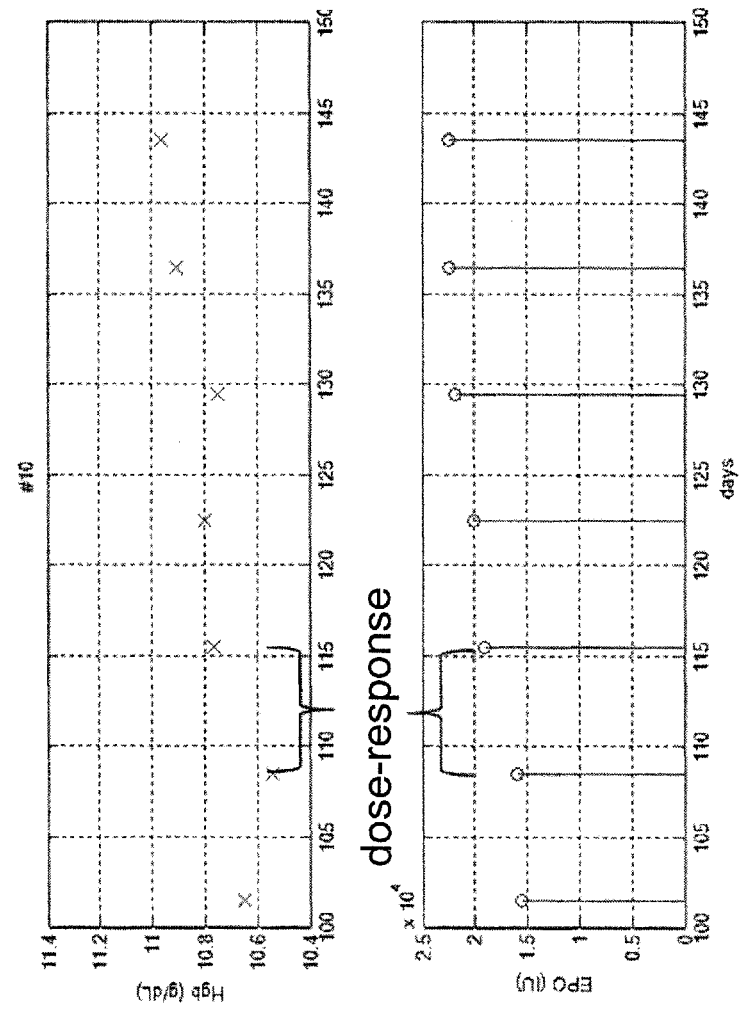
FIG. 4 shows certain EPO dose computation approaches.
Figure 5:
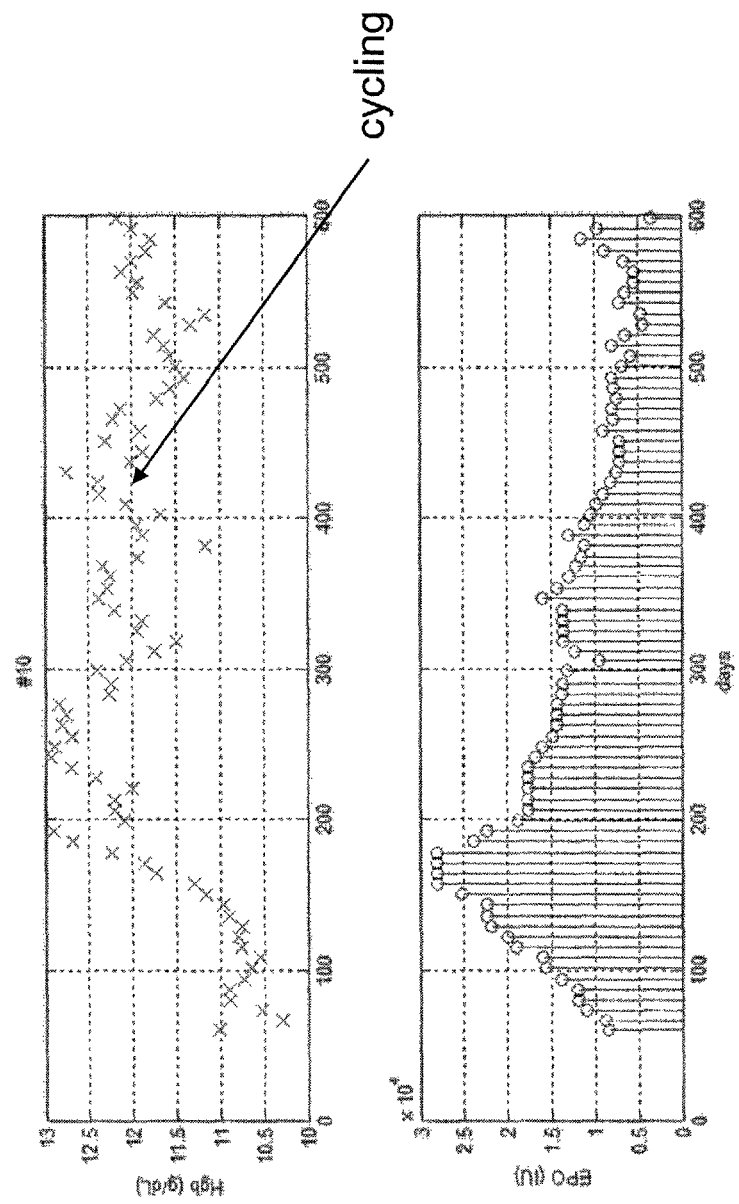
FIG. 5 shows resulting Hgb cycling due to incorrect AMP design.

Typical anemia management protocols are designed from a viewpoint where the designer (i.e., doctor) is too close to the treatment: the designer obtains an Hgb measurement, then makes an EPO dose decision. For instance, once a new Hgb measurement is obtained, the designer determines the next dose of ESA based on the expected dose-response behavior, e.g., based on how the designer predicts that the subject will respond to this dose as illustrated in FIG. 4. This is common to virtually all drug dosing protocols. However, in this approach, the designer cannot "see" the overall feedback system for the cause-effect relationship of EPO-to-Hgb (e.g., as implemented by a controller as is discussed in various embodiments herein). Thus, the designer in such prior art systems can only observe a 'local' viewpoint, and has no way of accounting for other effects, such as the relationship between the ESA and the resulting Hgb concentration, especially with respect to time. However, when drug dosing is done on a repetitive nature, the resulting Hgb dynamics are often different from the 'designer's dose-response understanding, no matter how accurate this understanding is, and thus, the resulting predictions will be lead astray (see FIG. 5 and resulting Hgb cycling due to incorrect design). However, this problem has not previously been recognized, and many designers or doctors continue to make predictions based only on expected (or guessed) dose-response behavior, and do not take into account the relationship between the previous dose of the ESA and the resulting Hgb concentration.

Figure 6:
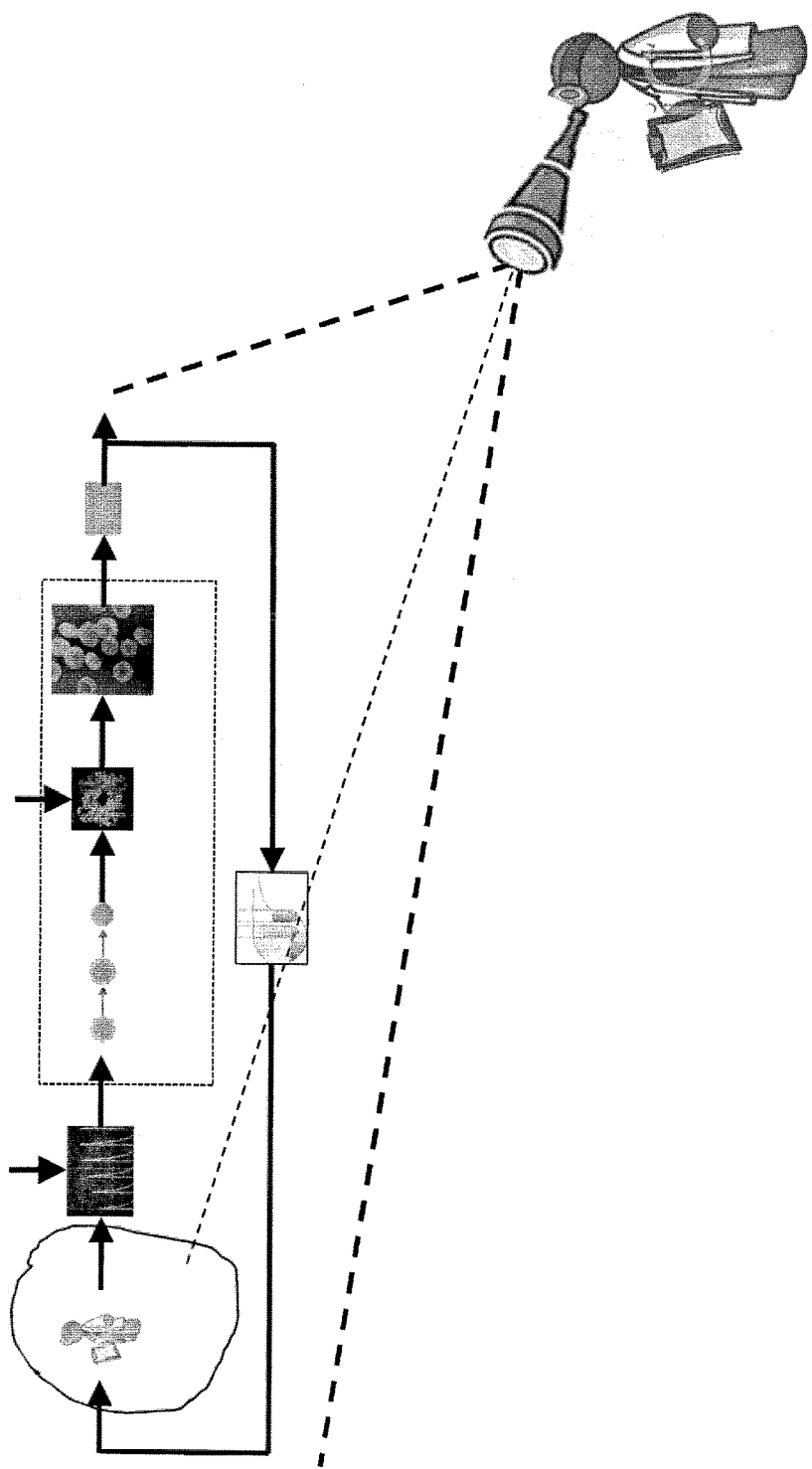
FIG. 6 shows a schematic view of an optimal approach for AMP design in accordance with certain embodiments of the invention.

Accordingly, in some embodiments, the present invention is generally directed to a "large view" of dynamic feedback interaction, e.g., to account for this relationship, as schematically suggested in FIG. 6. The invention, in some embodiments, recognizes that a new system is created through feedback, and by taking into account the relationship the previous dose of the ESA and the resulting Hgb concentration, e.g., via a controller, more optimal dosing of an ESA may be achieved in a subject. To illustrate this, the systems and methods described in the following non-limiting examples are designed based on short and long-term performance objectives such as avoiding overshooting and gaining stability. Performance tradeoffs are evaluated a priori as a function of modeling fidelity.

Figure 11:
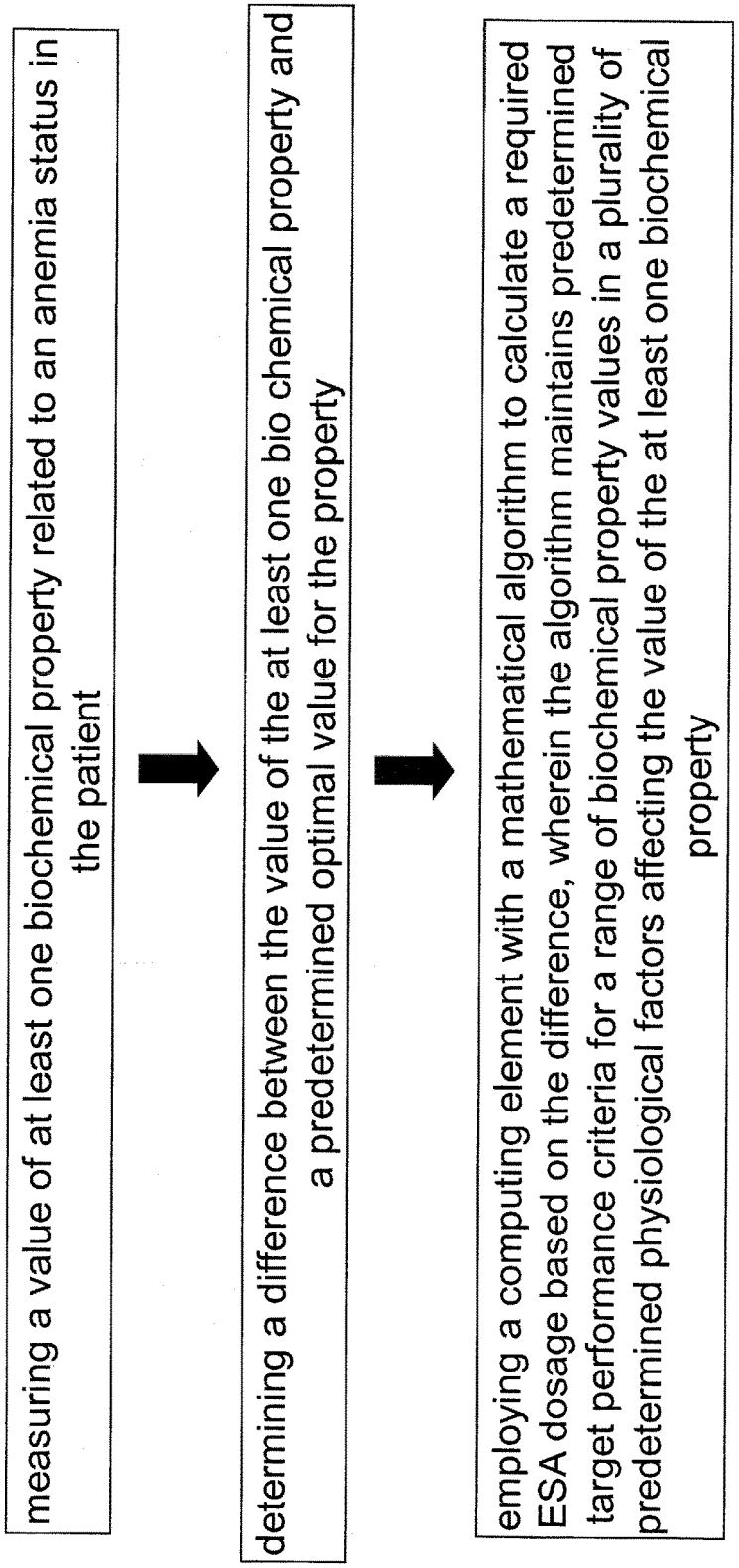
FIG. 11 shows a method associated with an embodiment of the present invention.

Attention is now turned to FIG. 11 which shows a non-limiting embodiment of the present invention, describing a method for computing erythropoiesis-stimulating agents (ESAs) dosing (e.g., intravenously, subcutaneously, orally, etc.), for treating anemia in a subject, such as a human subject, including the following steps: measuring a value of at least one biochemical property related to an anemia status in the subject; determining a difference between the value of the at least one biochemical property and a predetermined optimal value for the property; and, employing a computing element with a mathematical algorithm to calculate a required ESA dosage based on the difference, wherein the algorithm maintains predetermined target performance criteria for a range of biochemical property values in a plurality of predetermined physiological factors affecting the value of the at least one biochemical property.

A plurality of predetermined physiological factors may be used, including the lifespan of red blood cells in the range of 20-200 days, mean corpuscular hemoglobin (MCH) in the range of 25-42 picograms/cell, and the time from ESA stimulation to release of new red blood cell into circulation in the range of 3-9 days. The biochemical property most usually measured is the concentration of hemoglobin, although other properties could also be used in other embodiments. Deviations from ideality for hemoglobin concentration allow for determination of appropriate ESA dosing for a subject. In this embodiment, the algorithm has a fixed value for a range of hemoglobin concentration values, generally but not necessarily, 8 to 14 g/dl of blood.

Figure 12:
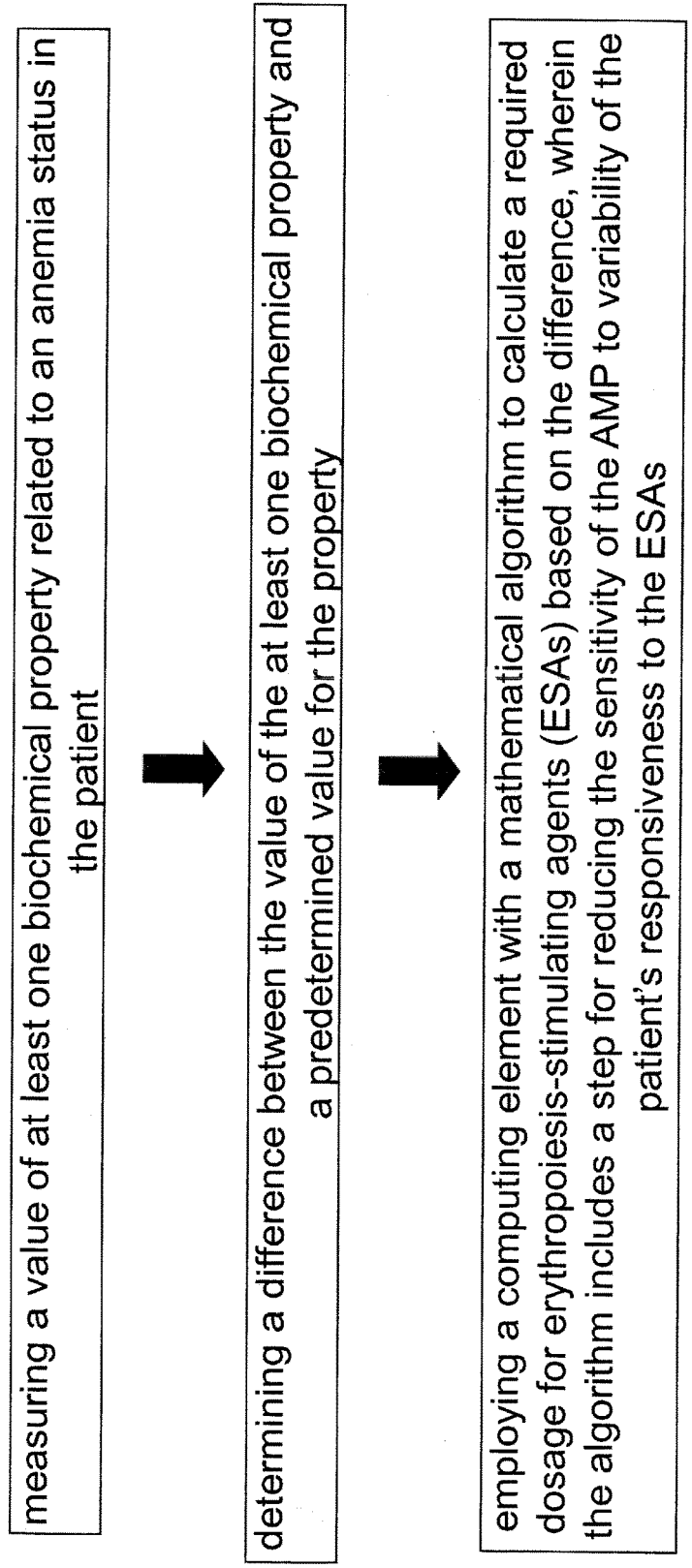
FIG. 12 shows a method associated with another embodiment of the present invention.

Attention is now turned to FIG. 12, where is described another non-limiting embodiment of a method for applying an Anemia Management Protocol (AMP) for treating anemia in a subject, such as a human subject, including: measuring a value of at least one biochemical property related to an anemia status in the subject; determining a difference between the value of the at least one biochemical property and a predetermined value for the property; and, employing a computing element with a mathematical algorithm to calculate a required dosage for erythropoiesis-stimulating agents (ESAs) based on the difference, wherein the algorithm includes a step for reducing the sensitivity of the AMP to the variability in the subject's responsiveness to the ESAs.

Figure 13:
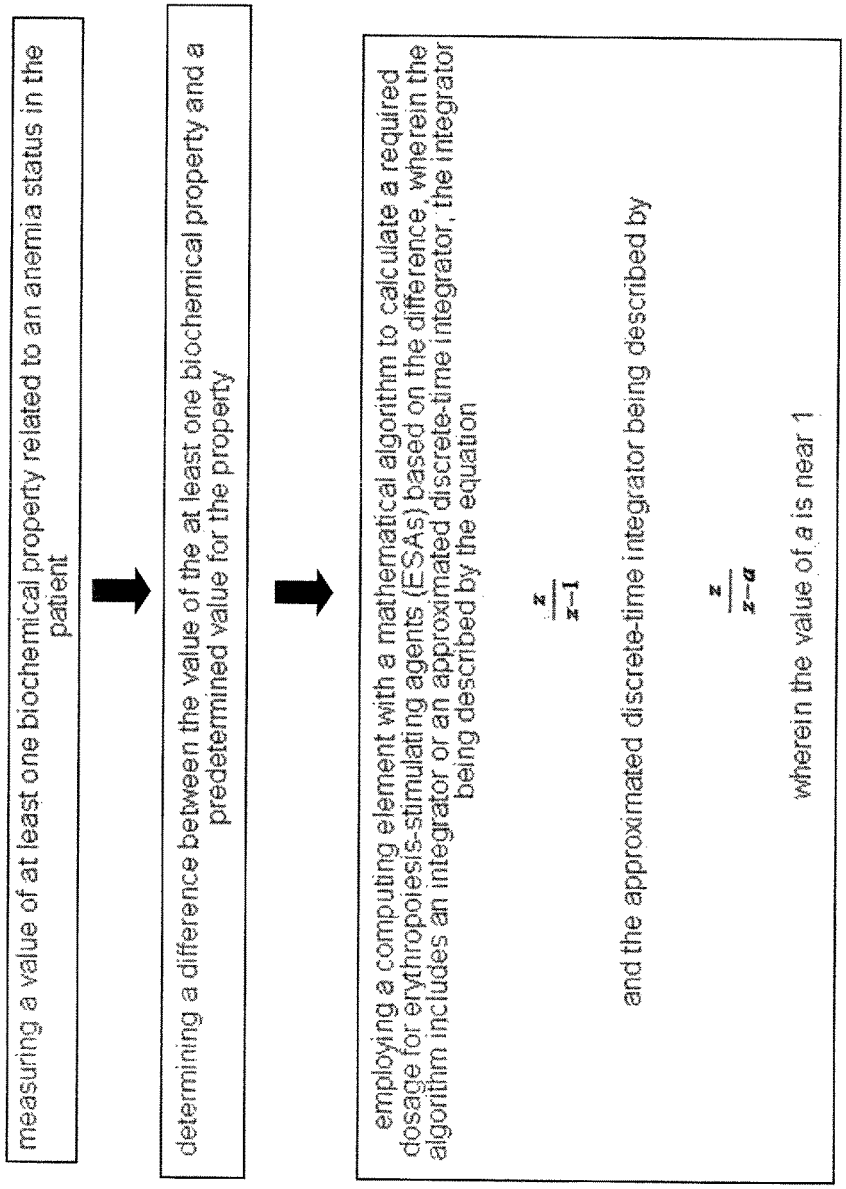
FIG. 13 shows a method associated with another embodiment of the present invention.

Attention is now turned to FIG. 13 which describes yet another non-limiting embodiment of a method for applying an Anemia Management Protocol (AMP) for treating anemia in a human subject, including: measuring a value of at least one biochemical property related to an anemia status in the subject; determining a difference between the value of the at least one biochemical property and a predetermined value for the property; and, employing a computing element with a mathematical algorithm to calculate a required dosage for erythropoiesis-stimulating agents (ESAs) based on the difference.

In some cases, the algorithm may include an integrator or an approximated discrete-time integrator, the integrator being described by the equation:

$$\frac{z}{z-1},$$

and the approximated discrete-time integrator being described by:

$$\frac{z}{z-a},$$

wherein the value of a is selected to be near 1. The variable z is defined so that $z^{-1}$ denotes a unit sample time delay. That is, at the sample time kT the integrator output y(kT) is related to the current input signal u(kT) by the difference equation:

$$y(kT)=u(kT)+y(kT-T),$$

where y(kT−T) is the output signal in the previous sample time. Accordingly, if the integrator output is the concentration of a suitable erythropoiesis-stimulating agent and the input signal is hemoglobin concentration, then the above equation may be used to capture their relationship.

Figure 14:
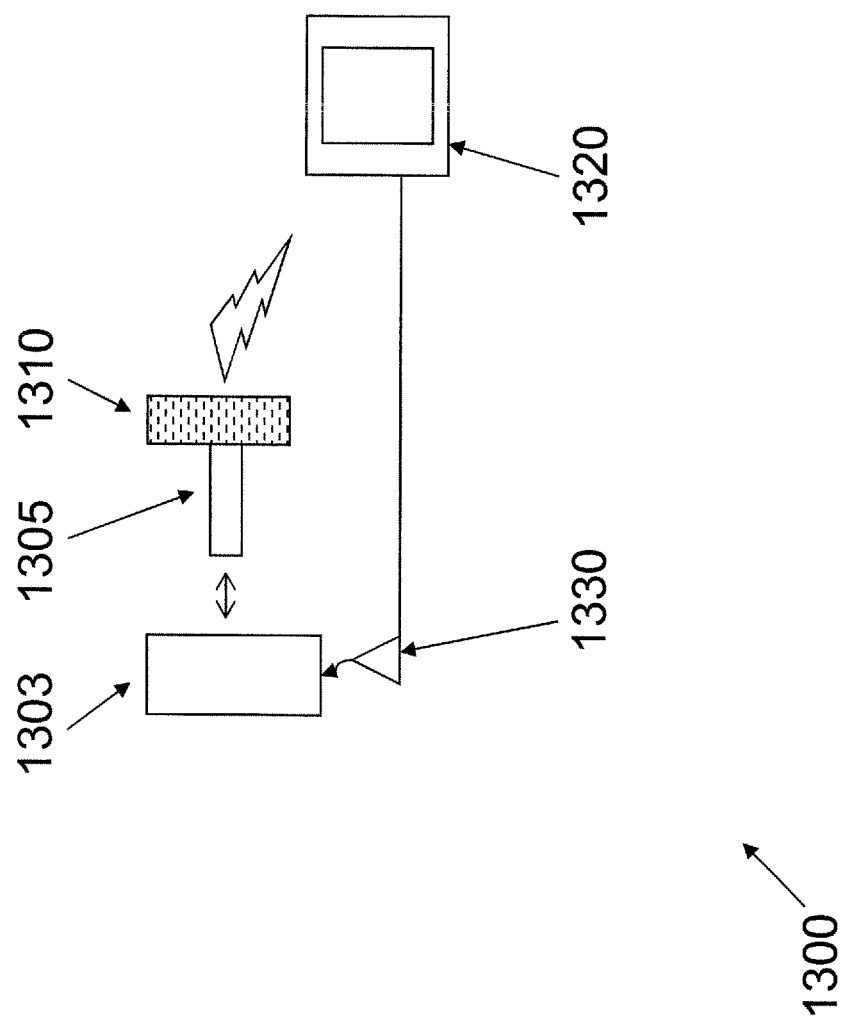
FIG. 14 shows a schematic view of a device associated with an embodiment of the instant invention.

Attention is now turned to FIG. 14 which shows a schematic view of non-limiting example device 1300 for delivering an optimized amount of an erythropoiesis-stimulating agents (ESAs) (e.g., intravenously, subcutaneously, orally, etc.), for treating anemia in a human subject 1303, including: a measuring element 1305 adapted to measure a value of at least one biochemical property related to an anemia status in the subject; a communication element 1310 adapted to communicate the value to a computing element 1320 adapted to calculate a difference between the value of said at least one biochemical property and a predetermined value or range of values for the property, the element adapted to employ a mathematical algorithm to calculate a required ESA dosage based on the difference, wherein the algorithm remains fixed for a predetermined range of target values of the property; and, optionally, a delivery element 1330 for delivering said ESA to the subject 1303. For example, delivery element 1330 may include a needle, such as a hypodermic needle, and a reservoir containing the ESA.

In most applications, the erythropoiesis-stimulating agent will be EPO, although other erythropoiesis-stimulating agents that could also be used (in addition to or instead of EPO) have been previously discussed herein. In some embodiments, the delivery element 1330 may be implanted directly into subject 1303. In some embodiments, the communication element 1310 includes wireless component for moving data between components of the device 1300. Any component of the device 1300 that comes into direct contact with subject 1300 or bodily fluids of subject 1303 may be disposable in certain cases. As non-limiting example, the computing element may be a laptop computer, a tablet computer, a cell phone, a table-top computer, a networked computing device, a wireless computing device, or the like.

As used herein the term "about" refers to +/−10%. As used herein, the singular form "a", "an" and "the" include plural references unless the context clearly dictates otherwise. For example, the term "a compound" or "at least one compound" may include a plurality of compounds, including mixtures thereof.

The following examples are intended to illustrate certain embodiments of the present invention, but do not exemplify the full scope of the invention.

Example 1

In this example, comparisons were made between a traditional EPO (erythropoietin) dosing protocol and a protocol based on an embodiment of the instant invention. The model as described in Equations 1-5 above was used in a simulation, with parameters estimated based on a retrospective data corresponding to 49 subjects collected over a period of 18 months. The typical protocol used in this example was a "one-size fits all" protocol, e.g., population-oriented and having a set of rules based on Hgb trending and Hgb ranges. Both protocols assumed weekly EPO dose adjustments with 3x/week administration. Protocol performance criteria were as follows:

Achieve $Hgb_{SS}$=11.25 g/dL at steady state.
Reduce overshooting
Robustness, i.e., to be effective for the entire set of models within that group.

Subjects were generally categorized based on their weekly use of EPO: hyper-responsive (<12000 IU/week), intermediate-responsive (between 12000 and 30000 IU/week), and hypo-responsive (>30000 IU/week). Another possible categorization was based on the steady-state gain of the subject's gain:

$$gain=0.295(\mu_{RBC})\bar{k}_{in}(d_{SS}),$$

where $\mu_{RBC}$ is the mean RBC lifespan in the subject (typically 20-200 days), $d_{SS}$ denotes the constant EPO dose required to yield a specified steady-state Hgb concentration $Hgb_{SS}$ in the subject, and $\bar{k}_{in}(d_{SS})$ denotes the mean production rate of new reticulocytes. $\bar{k}_{in}$ is discussed above in Equation 3. $d_{ss}$ may be computed using numerical simulations to compute the value of $d_{ss}$ that results in the desired target Hb. See also Nichols, et al., "Simplification of an erythropoiesis model for design of anemia management protocols in end stage renal disease," *Conf. Proc. IEEE Eng. Med. Biol. Soc.,* 2011:83-86, 2011, incorporated herein by reference in its entirety.

The subjects were categorized into four groups: hypo-responsive (gain<$8e^{-4}$), intermediate-responsive ($8e^{-4}$≤gain<$18e^{-4}$), hyper-responsive ($18e^{-4}$≤gain <$30.42e^{-4}$), and very hyper-responsive (gain≥$30.42e^{-4}$). ($8e^{-4}$~0.146, $18e^{-4}$~0.330, and $30.42e^{-4}$~0.557.) The following controllers were individualized for each group:

$$C(z) = \begin{cases} \frac{908.7(z-0.795)}{z-1} & \text{hypo responsive} \\ \frac{297.6(z-0.795)}{z-1} & \text{intermediate responsive} \\ \frac{140.2(z-0.795)}{z-1} & \text{hyper responsive} \\ \frac{74.1(z-0.795)}{z-1} & \text{very hyper responsive} \end{cases}$$

The variable z is defined so that $z^{-1}$ denotes a unit sample time delay. That is, at the sample time kT the controller's output y(kT) is related to the current input signal u(kT) (dose of the ESA, e.g., EPO) by the difference equation (shown here for the hypo responsive controller):

$$y(kT)=908.7(u(kT)-0.795u(kT-T))+y(kT-T),$$

where y(kT−T) is the output signal in the previous sample time. See also Nichols, et al., "Simplification of an erythropoiesis model for design of anemia management protocols in end stage renal disease," *Conf. Proc. IEEE Eng. Med. Biol. Soc.,* 2011:83-86, 2011, incorporated herein by reference in its entirety, for a discussion of responsiveness in subjects.

To study protocol performance under intrasubject variability, random variations were introduced in the response to EPO stimulation (0 mean, 0.05 SD). The performance requirements for the new protocol were all met: the target of Hgb of 11.25 g/dL was within the desired range and robustness. Performance comparisons between the new protocol and the traditional treatment demonstrated that in each of the groups, the new anemia management protocol outperformed the traditional anemia management protocol as shown in FIG. 7, where "New" refers to an embodiment of the instant invention and "Current" refers to a traditional protocol as generally applied. In particular, larger Hgb variability was observed with the traditional protocol. Finally, mean weekly EPO use with the traditional protocol was at least 10% greater (5.5% in very hyper-responsive) than that with the new protocol.

Example 2

Figure 8:
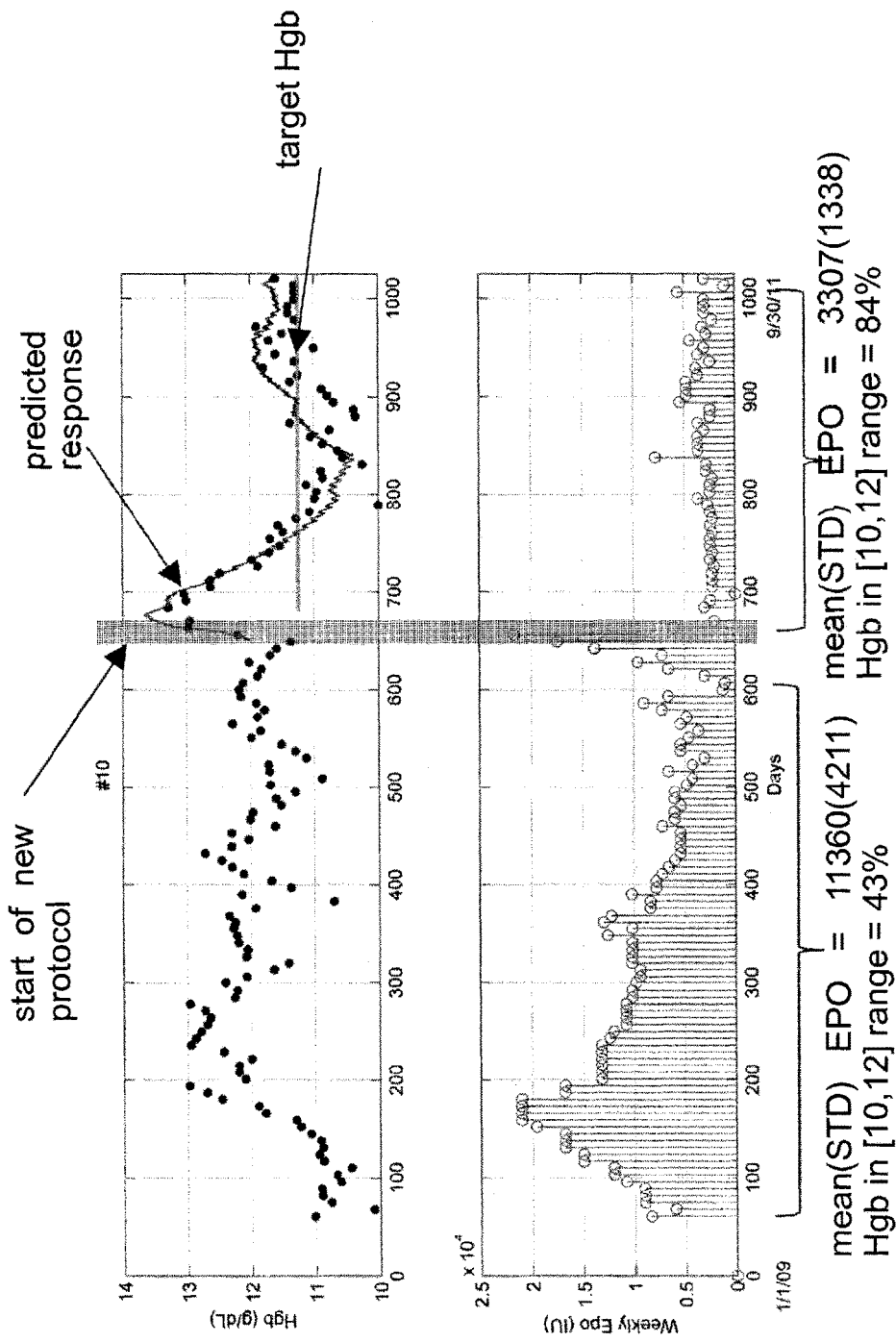
FIG. 8 shows clinical results related to the implementation of different AMPs, including one based on an embodiment of the present invention.

FIG. 8 shows clinical results related to the implementation of different anemia management protocols (AMPs) including one based on an embodiment of the present invention. Up to around day 670, EPO (erythropoietin) doses for a subject (#10) have been computed using several anemia management protocols. During this time period, undesirable Hgb (hemoglobin) cycling and a lack of Hgb remaining in a range were observed.

In contrast, a new anemia management protocol (implemented using one embodiment of the present invention) was switched on at day 670. It was found that the new protocol was able to smoothly guide the subject's Hgb to its target and maintain it within the target range. In all performance measures (data not shown), the new anemia management protocols outperformed the control anemia management protocols.

Example 3

In this example, to demonstrate that in order to improve the AMPs (anemia management protocols) performance as the dynamics of subjects vary with time, the gain of AMP may be adjusted whenever a change in the subject's responsiveness (the "gain") is detected. This change was studied in this example in one of two ways:

1. The subject moved from one responsiveness group to another, in which case, the controller may be updated according to the particular controllers for that group, or 2. The gain of the subject's controller is modified in proportion to the gain, for example, if the gain has increased by 20%, then the controller's gain is decreased by 20%.

Figure 9:
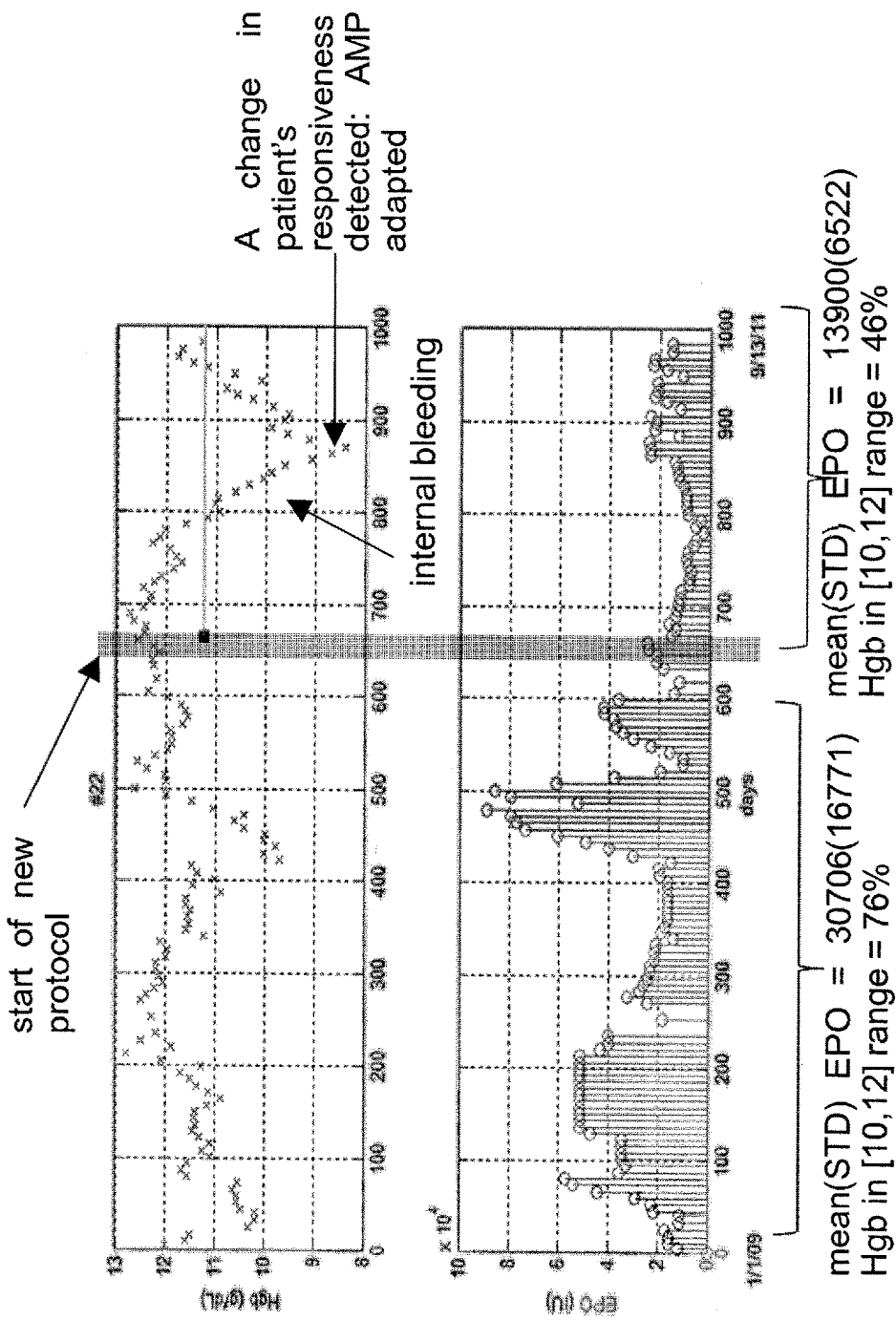
FIG. 9 shows clinical results related to the implementation of different AMPs, including one based on an embodiment of the present invention.

This individualization of the protocol as related to various embodiments of the present invention requires the estimation of a subject's responsiveness (i.e., the gain). There are several approaches that may be used for estimating this value, for example, least square estimation or the Kalman filter or one of its extensions. FIG. 9 illustrates such a case in a clinical study. Similar to the results in Example 2, up to around day 670, EPO (erythropoietin) doses for the subject have been computed using several AMPs. During this time period, undesirable Hgb (hemoglobin) cycling and a lack of Hgb remaining in a desired range were observed.

A new AMP (implemented using one embodiment of the present invention) was switched on at day 670. The new AMP was able to smoothly guide the subject's Hgb to its target. However, starting around day 800, the subject developed a slow internal bleeding that was completely overcome only two months later. The new protocol detected a corresponding change in the subject's responsiveness and adapted the AMP accordingly. The adaptation was successful and that the AMP overcame the bleeding and successfully guided Hgb to its target without cycling. In spite of this lengthy episode of bleeding, the new AMP (including adaptation to the subject's changing condition) outperformed traditional AMPs in terms of performance measures.

Example 4

Figure 10:
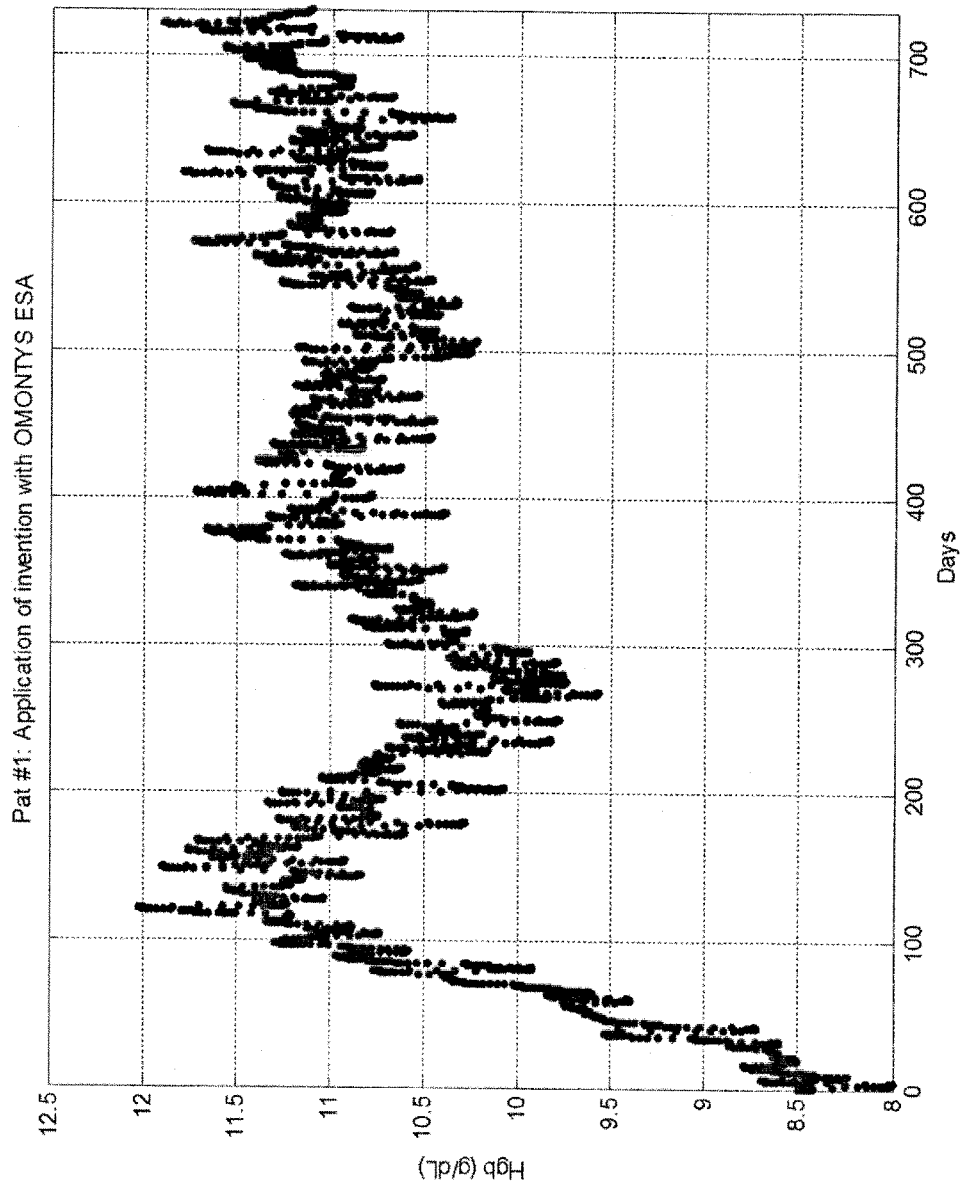
FIG. 10 shows simulated Hgb (hemoglobin) response of a patient using an anemia management protocol (AMP) design for an erythropoiesis-stimulating agent, OMONTYS.

This example demonstrates the applicability of an anemia management protocol (AMP) designed for the recently FDA-approved ESA OMONTYS made by Affimax. The basic pharmacokinetic/pharmacodynamics model estimated in Example 1 (see FIG. 1) was used in this example, and PK parameters were modified to reflect the mean drug half-life of 48 hours. The reported conversion of Epogen dose to OMONTYS dose was also used. The subject's endogenous Hgb was set to 8.5 g/d, and fluid variability was modeled using a multiplicative white noise of mean 1 and standard deviation of 0.023. The ability of the new AMP to guide the subject to its Hgb target of 11.25 g/l and stabilize it around that concentration with minimal cycling is demonstrated in FIG. 10.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for applying an Anemia Management Protocol (AMP) for treating anemia in a human subject, including:
   (a) measuring a value of at least one biochemical property related to an anemia status in said subject;
   (b) determining a difference between said value of said at least one biochemical property and a predetermined value for said property; and,
   (c) employing a device comprising a computing element with an individualized feedback algorithm to calculate a required dosage for erythropoiesis-stimulating agent (ESA) based on said difference, wherein said algorithm includes an integrator or an approximated discrete-time integrator, said integrator being described by the equation $$\frac{z}{z-1},$$

and said approximated discrete-time integrator being described by $$\frac{z}{z-a},$$

wherein the value of a is near 1;
   (d) administering the required dosage for the erythropoiesis-stimulating agent to the subject as calculated using the algorithm including the integrator or the approximated discrete-time integrator; and
   (e) repeating steps (a) through (d) a plurality times, such that the required dosage administered to the subject in step (d) varies with respect to time according to the algorithm including the integrator or the approximated discrete-time integrator.

2. The method according to claim 1, wherein said discrete-time integrator is selected from the group consisting of the Forward Euler method, the Backward Euler method, the Trapezoidal method, the second-order accurate method, or a higher-order method.

3. The method according to claim 1, wherein said algorithm includes a step for adjusting the gain of said AMP for a present level of said subject's responsiveness to said ESA.

4. The method according to claim 3, wherein said subject's responsiveness to said ESA is estimated using the following equation:

$$\text{estimated responsiveness} = \frac{\text{mean(weekly } Hgb \text{ measurements during past } n \text{ weeks})}{\text{mean(weekly } ESA \text{ doses during past } n \text{ weeks})}.$$

5. The method according to claim 4, wherein said gain associated with said AMP is adjustable in an inversely proportional manner to said responsiveness.

6. The method of claim 1, wherein the at least one biochemical property is hemoglobin.

7. A method comprising:
   (a) determining a hemoglobin concentration in a subject;
   (b) using a device comprising an individualized feedback controller comprising an integrator or an approximated discrete-time integrator, and encoding Equations 1-5, to determine a dosage of an erythropoiesis-stimulating agent;
   (c) administering the dosage to the subject as determined using the individualized feedback controller comprising the integrator or the approximated discrete-time integrator, encoding Equations 1-5; and
   (d) repeating steps (a) through (c) a plurality times, such that the dosage administered to the subject in step (c) varies with respect to time according to the individualized feedback controller comprising the integrator or the approximated discrete-time integrator, encoding Equations 1-5.

8. The method of claim 7, wherein the device administers the dosage to the subject.

9. The method of claim 7, wherein the device determines the hemoglobin concentration in the subject.

10. The method of claim 7, wherein the device comprises a hemoglobin sensor.

11. The method of claim 7, wherein the device is able to withdraw a sample of blood from the subject.

12. The method of claim 11, wherein the device determines hemoglobin within the sample of blood.

13. The method of claim 7, wherein the device comprises a needle and a reservoir containing the erythropoiesis-stimulating agent.

14. The method of claim 13, wherein the erythropoiesis-stimulating agent is erythropoietin.

15. The method of claim 13, wherein the erythropoiesis-stimulating agent is recombinant human erythropoietin.

16. The method according to claim 7, wherein said discrete-time integrator is selected from the group consisting of the Forward Euler method, the Backward Euler method, the Trapezoidal method, the second-order accurate method, or a higher-order method.

17. The method according to claim 7, wherein said controller encodes a step for adjusting the gain of said AMP for a present level of said subject's responsiveness to said ESA.

18. The method according to claim 17, wherein said subject's responsiveness to said ESA is estimated using the following equation:

$$\text{estimated responsiveness} = \frac{\text{mean(weekly } Hgb \text{ measurements during past } n \text{ weeks)}}{\text{mean(weekly } ESA \text{ doses during past } n \text{ weeks)}}.$$

19. The method according to claim 18, wherein said gain associated with said AMP is adjustable in an inversely proportional manner to said responsiveness.

20. The method according to claim 7, wherein the individualized feedback controller is able to maintain the hemoglobin concentration between 8 g/dl and 14 g/dl.

21. A device, comprising:
a receiver for determining a hemoglobin concentration in a subject;
an individualized feedback controller comprising an integrator or an approximated discrete-time integrator, and encoding Equations 1-5 to determine a dosage of an erythropoiesis-stimulating agent using the hemoglobin concentration; and
an applicator for administrating the dosage to the subject as determined using the individualized feedback controller comprising the integrator or the approximated discrete-time integrator, encoding Equations 1-5.

22. The device of claim 21, wherein the applicator comprises a needle.

23. The device of claim 21, wherein the receiver further comprises a hemoglobin sensor.

24. The method according to claim 21, wherein the individualized feedback controller is able to maintain the hemoglobin concentration between 8 g/dl and 14 g/dl.

* * * * *